(12) United States Patent
Jung et al.

(10) Patent No.: US 11,920,118 B2
(45) Date of Patent: Mar. 5, 2024

(54) METHOD FOR FABRICATING HIGHLY ELASTIC POROUS POLYMER MEMBRANE, METHOD FOR MANUFACTURING CELL CULTURE SYSTEM USING POROUS POLYMER MEMBRANE FABRICATED BY THE FABRICATION METHOD AND CELL CULTURE SYSTEM MANUFACTURED BY THE MANUFACTURING METHOD

(71) Applicant: KOREA INSTITUTE OF SCIENCE AND TECHNOLOGY, Seoul (KR)

(72) Inventors: Young Mee Jung, Seoul (KR); Soo Hyun Kim, Seoul (KR); Justin Jihong Chung, Seoul (KR); Jin Yoo, Seoul (KR); Tae Hee Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 654 days.

(21) Appl. No.: 17/081,723

(22) Filed: Oct. 27, 2020

(65) Prior Publication Data

US 2021/0301241 A1 Sep. 30, 2021

(30) Foreign Application Priority Data

Mar. 30, 2020 (KR) .......................... 10-2020-0038224

(51) Int. Cl.
*C12M 1/00* (2006.01)
(52) U.S. Cl.
CPC ............ *C12M 29/04* (2013.01); *C12M 23/26* (2013.01)
(58) Field of Classification Search
CPC ............................... C12M 29/04; C23M 23/26
See application file for complete search history.

(56) References Cited

U.S. PATENT DOCUMENTS

| 2007/0071790 A1* | 3/2007 | Ameer | A61L 27/58 424/423 |
|---|---|---|---|
| 2018/0264474 A1* | 9/2018 | Livermore | B01L 3/502715 |
| 2018/0326362 A1* | 11/2018 | Niu | B01D 69/12 |

FOREIGN PATENT DOCUMENTS

| KR | 100558578 B1 | 3/2006 |
| KR | 20150059620 A1 * | 6/2015 |
| KR | 10-1621173 B1 | 5/2016 |

OTHER PUBLICATIONS

Bong Jun Cha et al., "Polymeric Membranes for Water Treatment", Dec. 1, 2011.

* cited by examiner

*Primary Examiner* — Dah-Wei D. Yuan
*Assistant Examiner* — Kristen A Dagenais
(74) *Attorney, Agent, or Firm* — Rabin & Berdo, P.C.

(57) ABSTRACT

Provided are a method for fabricating a highly elastic porous polymer membrane, a method for manufacturing a cell culture system using a porous polymer membrane fabricated by the fabrication method, and a cell culture system manufactured by the manufacturing method. The porous polymer membrane can be fabricated by spin coating a mixture solution containing a biodegradable elastomeric polymer and a water-soluble moisture absorbent in an optimum ratio while maintaining a high relative humidity. The porous polymer membrane has a uniform thickness and a uniform pore size and is highly elastic. In addition, the thickness and pore size of the porous polymer membrane can be controlled. The porous polymer membrane can induce active cell-cell interaction during cell co-culture due to its high porosity. The porous polymer membrane enables control over cell alignment or array due to its high biocompatibility and elasticity. The porous polymer membrane can be utilized (Continued)

in a platform for inducing stem cell differentiation, a lab-on-a-chip, a synthetic skin simulant platform, etc.

9 Claims, 7 Drawing Sheets

METHOD FOR FABRICATING HIGHLY ELASTIC POROUS POLYMER MEMBRANE, METHOD FOR MANUFACTURING CELL CULTURE SYSTEM USING POROUS POLYMER MEMBRANE FABRICATED BY THE FABRICATION METHOD AND CELL CULTURE SYSTEM MANUFACTURED BY THE MANUFACTURING METHOD

CROSS-REFERENCE TO RELATED APPLICATIONS

This application claims priority under 35 U.S.C. § 119 to Korean Patent Application No. 10-2020-0038224 filed on Mar. 30, 2020 in the Korean Intellectual Property Office, the disclosure of which is incorporated herein by reference in its entirety.

BACKGROUND OF THE INVENTION

1. Field of the Invention

The present invention relates to a method for fabricating a highly elastic porous polymer membrane, a method for manufacturing a cell culture system using a porous polymer membrane fabricated by the fabrication method, and a cell culture system manufactured by the manufacturing method.

2. Description of the Related Art

Cells in tissues incessantly interact with the surrounding cells and the extracellular matrix (ECM) to maintain the functions and homeostasis of the tissues. Homotypic cell-cell interaction or heterotypic cell-cell interaction is known as an important mechanism that is involved in tissue development and immune induction in vivo, wound healing, the maintenance and differentiation of stem cells, etc. Living cells communicate with each other either through direct contact (contact-dependent stimulus) or exchange of water-soluble factors (soluble stimulus), i.e. indirect contact via cytokines, chemokines, and growth factors.

Co-culture is a typical method for regulating the functions of specific cells through cell interaction. The importance of co-culture platforms has emerged also in the field of tissue engineering where an in vitro environment simulating an in vivo environment is used to investigate intercellular signaling mechanisms or is again implanted in vivo for use. As well, co-culture platforms can induce the differentiation of stem cells into various cells, including neurons, myocardiocytes, chondrocytes, and blood cells, in vitro through co-culture with stromal cells.

However, co-culture of different cell types always involves cross-contamination between the cells and resulting adverse effects. Further, exponential proliferation of a certain cell type makes it difficult to induce interaction with other cell types at a constant level. In attempts to solve the above problems, cell co-culture platforms including a porous membrane separating different cell types have been introduced.

However, commercially available membrane-based co-culture systems have limitations in that their low porosity and micrometer-scale thickness hinder cells from actively interacting with each other and their inelasticity makes it impossible to align cells alignment. Lung-on-a-chip systems essentially requires flexible co-culture membranes. Most studies have focused on flexible co-culture membranes using polydimethylsiloxane (PDMS) and only a few studies have been done on elastic co-culture membranes.

Korean Patent No. 10-1621173 discloses the fabrication of a nano-scale porous membrane using a polymer such as cellulose acetate through relative humidity control by non-solvent vapor induced phase separation. However, the porous membrane is not flexible, limiting its use. Further, the porous membrane is not biodegradable, limiting its use as a bio material.

SUMMARY OF THE INVENTION

The present invention has been made in an effort to solve the above problems, and one object of the present invention is to provide a highly elastic porous polymer membrane that has a uniform thickness and a uniform pore size.

A further object of the present invention is to provide a porous polymer membrane on which active cell-cell interaction can occur during cell co-culture.

Another object of the present invention is to provide a scaffold for cell culture including the porous polymer membrane.

Another object of the present invention is to provide a cell culture system including the scaffold for cell culture that enables control over cell alignment or array due to its high biocompatibility and elasticity.

Still another object of the present invention is to provide a method for manufacturing a cell culture system using the porous polymer membrane.

The objects of the present invention are not limited to the above-mentioned ones. The objects of the present invention will become more apparent from the following detailed description and will be implemented by means described in the claims and a combination thereof.

The present invention provides a method for fabricating a porous polymer membrane, including: mixing a biodegradable elastomeric polymer with a water-soluble moisture absorbent in an organic solvent to prepare a mixture solution; and applying the mixture solution to a substrate in a closed chamber, followed by spin coating at a relative humidity of 65 to 90%.

The biodegradable elastomeric polymer may be selected from the group consisting of poly(L-lactide-co-caprolactone), poly(L-lactide-co-glycolide), poly(L-lactide-co-D-lactide), polylactide, polycaprolactone, polyglycolide, polyethylene glycol, and mixtures thereof.

The water-soluble moisture absorbent may be selected from the group consisting of LiCl, $CaCl_2$, $ZnCl_2$, KOH, NaOH, $MgCl_2$, $FeCl_3$, $K_2CO_3$, and mixtures thereof.

The organic solvent may be selected from the group consisting of tetrahydrofuran, dimethylformamide, diethylformamide, N-methyl-2-pyrrolidone, dimethyl sulfoxide, dimethylacetamide, methanol, ethanol, chloroform, dichloromethane, and mixtures thereof.

The biodegradable elastomeric polymer may be mixed with the water-soluble moisture absorbent in a weight ratio of 1:0.05-0.4 in the organic solvent to prepare the mixture solution.

The relative humidity may be adjusted to 70 to 85% with a supersaturated salt solution.

The spin coating may be performed at a speed of 1000 to 4000 rpm for 10 seconds to 1 minute.

The porous polymer membrane may have a thickness of 300 nm to 3 µm, a pore size of 100 nm to 5 µm, and a porosity of 20 to 80%.

The biodegradable elastomeric polymer may be poly(L-lactide-co-caprolactone), poly(L-lactide-co-glycolide) or a mixture thereof, the water-soluble moisture absorbent may be LiCl, the organic solvent may be tetrahydrofuran, the biodegradable elastomeric polymer may be mixed with the water-soluble moisture absorbent in a weight ratio of 1:0.1-0.3 in the organic solvent to prepare the mixture solution, the relative humidity may be adjusted to 74 to 76% with a supersaturated salt solution, the spin coating may be performed at a speed of 2800 to 3400 rpm for 20 seconds to 40 seconds, and the porous polymer membrane may have a thickness of 700 nm to 960 nm, a pore size of 900 nm to 1.2 μm, and a porosity of 35 to 45%.

The biodegradable elastomeric polymer may be poly(L-lactide-co-caprolactone), the water-soluble moisture absorbent may be LiCl, the organic solvent may be tetrahydrofuran, the biodegradable elastomeric polymer may be mixed with the water-soluble moisture absorbent in a weight ratio of 1:0.2 in the organic solvent to prepare the mixture solution, the relative humidity may be adjusted to 75% with a supersaturated salt solution, the spin coating may be performed at a speed of 3000 rpm for 30 seconds, and the porous polymer membrane may have a thickness of 960 nm, a pore size of 1 μm, and a porosity of 37%.

The present invention also provides a porous polymer membrane fabricated by mixing a biodegradable elastomeric polymer with a water-soluble moisture absorbent in an organic solvent to prepare a mixture solution, applying the mixture solution to a substrate in a closed chamber, followed by spin coating at a relative humidity of 65 to 90% wherein the porous polymer membrane has a thickness of 300 nm to 3 μm, a pore size of 100 nm to 5 μm, and a porosity of 20 to 80%.

The porous polymer membrane may be used for medical application, cell culture or aesthetic application.

The present invention also provides a scaffold for cell culture including the porous polymer membrane.

The present invention also provides a cell culture system including the scaffold for cell culture.

The present invention also provides a method for manufacturing a cell culture system, including: mixing a biodegradable elastomeric polymer with a water-soluble moisture absorbent in an organic solvent to prepare a mixture solution; applying the mixture solution to a substrate in a closed chamber, followed by spin coating at a relative humidity of 65 to 90% to fabricate a porous polymer membrane; removing the water-soluble moisture absorbent contained in the porous polymer membrane; stretching the porous polymer membrane from which the water-soluble moisture absorbent is removed; and placing the stretched porous polymer membrane on cells.

The water-soluble moisture absorbent may be removed from the porous polymer membrane by impregnating the porous polymer membrane with water to dissolve the water-soluble moisture absorbent.

The porous polymer membrane may be stretched to a strain of 30 to 60% at a temperature of 20 to 40° C.

The porous polymer membrane of the present invention can be fabricated by spin coating a mixture solution containing a biodegradable elastomeric polymer and a water-soluble moisture absorbent in an optimum ratio while maintaining a high relative humidity and has a high porosity, a uniform thickness, and a uniform pore size and is highly elastic.

In addition, the thickness and pore size of the porous polymer membrane according to the present invention can be controlled. The porous polymer membrane of the present invention can induce active cell-cell interaction during cell co-culture due to its high porosity. The porous polymer membrane of the present invention enables control over cell alignment or array due to its high biocompatibility and elasticity. The porous polymer membrane of the present invention can be utilized in a platform for inducing stem cell differentiation, a lab-on-a-chip, a synthetic skin simulant platform, etc.

The effects of the present invention are not limited to the above-mentioned ones. It is should be understood that the effects of the present invention include all effects inferable from the following detailed description.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

The present invention will now be described in more detail as one embodiment.

The term "relative humidity" as used herein refers to the concentration of water vapor in air and is defined as the ratio of the partial pressure of water vapor in the mixture to the saturated vapor pressure of water at the same temperature. Relative humidity is normally expressed as a percentage.

The term "phase separation" as used herein refers to the transformation of a homogenous system (e.g., dope formulation) into two or more phases. In the present invention, the phase separation is performed based on the mechanism of vapor induced phase separation (VIPS).

The present invention is directed to a method for fabricating a highly elastic porous polymer membrane, a method for manufacturing a cell culture system using a porous polymer membrane fabricated by the fabrication method, and a cell culture system manufactured by the manufacturing method.

More specifically, the present invention provides a method for fabricating a porous polymer membrane, including: mixing a biodegradable elastomeric polymer with a water-soluble moisture absorbent in an organic solvent to prepare a mixture solution; and applying the mixture solution to a substrate in a closed chamber, followed by spin coating at a relative humidity of 65 to 90%.

Existing porous polymer membranes for co-culture systems fail to induce cell-cell interaction due to their low porosity and micrometer-scale large thickness. Further, polymer membranes using a polymer such as cellulose acetate suffer from difficulty in controlling cell array or alignment due to the inherent inelasticity of the polymer. The present inventors have conducted research to solve the problems of existing porous polymer membranes, and as a result, found that a highly elastic porous polymer membrane can be fabricated by spin coating a mixture solution containing a biodegradable elastomeric polymer and a water-soluble moisture absorbent while maintaining a high relative humidity. The present invention has been accomplished based on this finding.

Figure 1:
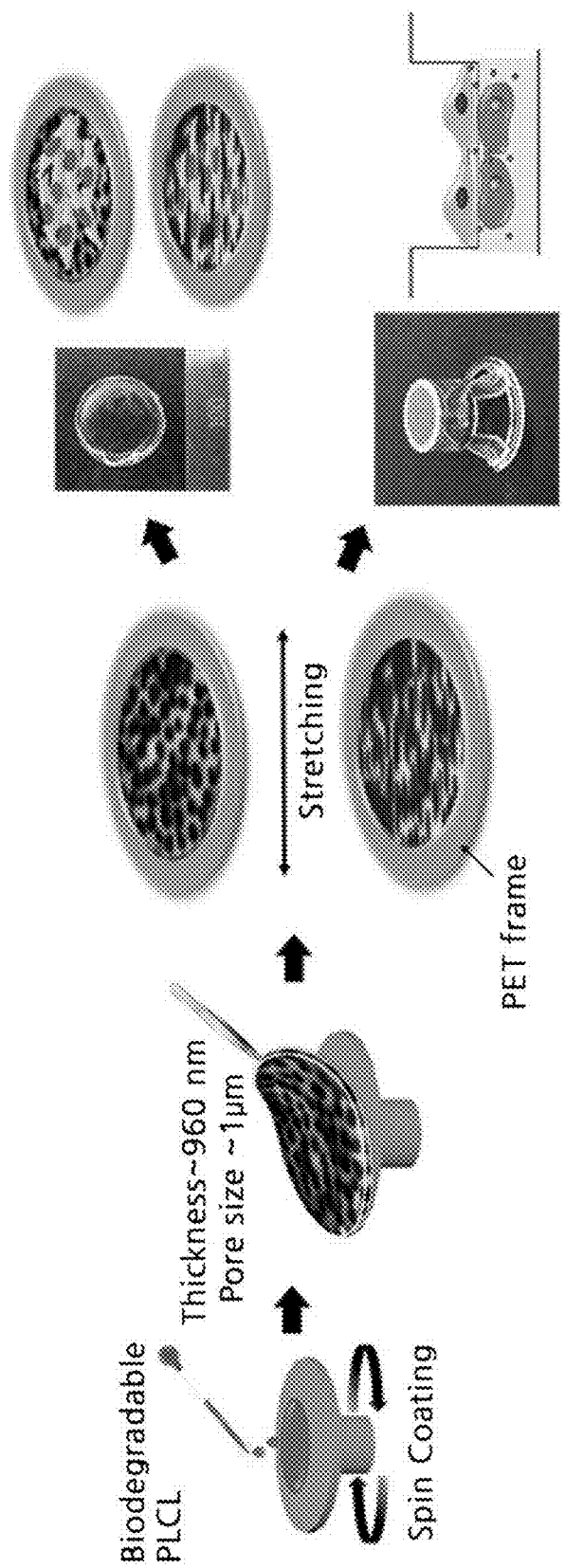
FIG. 1 is a schematic diagram showing a method for fabricating a porous polymer membrane according to the present invention and applications of a porous polymer membrane fabricated by the method.

FIG. 1 is a schematic diagram showing the method for fabricating a porous polymer membrane according to the present invention and applications of a porous polymer membrane fabricated by the method. Referring to FIG. 1, a mixture solution containing a biodegradable elastomeric polymer and a water-soluble moisture absorbent is applied to a substrate in a closed chamber, followed by spin coating to fabricate a porous polymer membrane. After removal of the water-soluble moisture absorbent, the porous polymer membrane is stretched. The stretched porous polymer membrane is applied to a cell culture scaffold (top) or a cell culture system (bottom).

Figures 2, 3:
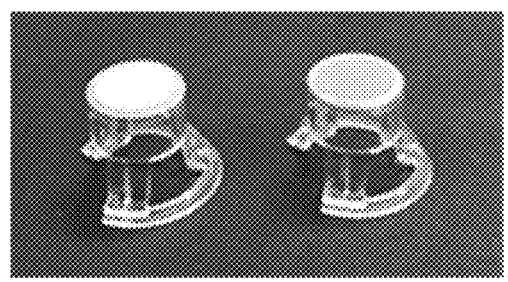
FIG. 2 is an image comparing an existing commercial co-culture membrane (left) with a porous membrane fabricated in Example 1 (right)
FIG. 3 shows SEM images showing the surface morphologies of porous polymer membranes fabricated in Examples 1 and 2 and Comparative Examples 1-1, 1-2, and 2-1 to 2-4.

FIG. 2 is an image comparing an existing commercial co-culture membrane (left) with a porous membrane fabricated in Example 1 (right). Referring to FIG. 2, the existing commercial co-culture membrane has a thickness of about 10 μm and is opaque white in color, whereas the porous polymer membrane fabricated in Example 1 is translucent due to its small thickness (~1 μm) compared to that of the existing co-culture membrane. Due to its small thickness, the porous polymer membrane fabricated in Example 1 can more actively induce cell-cell interaction than the existing co-culture membrane.

Specifically, the biodegradable elastomeric polymer used to prepare the mixture solution has physical properties similar to those of the skin due to its elasticity and is excellent in stretchability and biocompatibility. However, when it is desired to fabricate the porous polymer membrane based on vapor induced phase separation, phase separation cannot be induced even at a high relative humidity because of the very high hydrophobicity of the biodegradable elastomeric polymer. Thus, the porous polymer membrane is fabricated by vapor induced phase separation after mixing the water-soluble moisture absorbent with the biodegradable elastomeric polymer.

The biodegradable elastomeric polymer may have a glass transition temperature ($T_g$) of −20 to 20° C. and a weight average molecular weight (Mw) of 50,000 to 800,000 g/mol and may exhibit elastomeric properties at room temperature. Specifically, the biodegradable elastomeric polymer can be selected from the group consisting of poly(L-lactide-co-caprolactone), poly(L-lactide-co-glycolide), poly(L-lactide-co-D-lactide), polylactide, polycaprolactone, polyglycolide, polyethylene glycol, and mixtures thereof. Preferably, the biodegradable elastomeric polymer is selected from the group consisting of poly(L-lactide-co-caprolactone), poly (L-lactide-co-glycolide), poly(L-lactide-co-D-lactide), and mixtures thereof. More preferably, the biodegradable elastomeric polymer is poly(L-lactide-co-caprolactone), poly(L-lactide-co-glycolide) or a mixture thereof. Most preferably, the biodegradable elastomeric polymer is poly(L-lactide-co-caprolactone) (PLCL).

The molar ratio of L-lactide to caprolactone in the PLCL may be 1-9:9-1. The PLCL may have a number average molecular weight (Mn) of 50,000 to 500,000 g/mol and a weight average molecular weight (Mw) of 50,000 to 800,000 g/mol. When the molar ratio, the number average molecular weight, and the weight average molecular weight are in the respective ranges defined above, PLCL has high elasticity similar to the human skin.

The water-soluble moisture absorbent may be selected from the group consisting of LiCl, $CaCl_2$, $ZnCl_2$, KOH, NaOH, $MgCl_2$, $FeCl_3$, $K_2CO_3$, and mixtures thereof. Preferably, the water-soluble moisture absorbent is selected from the group consisting of LiCl, $CaCl_2$, $ZnCl_2$, and mixtures thereof. Most preferably, the water-soluble moisture absorbent is LiCl. The water-soluble moisture absorbent induces the biodegradable elastomeric polymer to sufficiently absorb the surrounding moisture or water at a high relative humidity during spin coating of the mixture solution applied to the substrate. That is, the water-soluble moisture absorbent allows phase separation to occur easily.

The organic solvent may be selected from the group consisting of, but not limited to, tetrahydrofuran, dimethylformamide, diethylformamide, N-methyl-2-pyrrolidone, dimethyl sulfoxide, dimethylacetamide, methanol, ethanol, chloroform, dichloromethane, and mixtures thereof. The organic solvent is preferably selected from the group consisting of tetrahydrofuran, dimethylformamide, N-methyl-2-pyrrolidone, and mixtures thereof. Tetrahydrofuran is most preferred as the organic solvent.

The biodegradable elastomeric polymer may be mixed with the water-soluble moisture absorbent in a weight ratio of 1:0.05-0.4, preferably 1:0.1-0.3, more preferably 1:0.15-0.25, most preferably 1:0.2, in the organic solvent to prepare the mixture solution. If the ratio of the biodegradable elastomeric polymer to the water-soluble moisture absorbent is 1: <0.05, the hydrophobicity of the biodegradable elastomeric polymer may be made strong, and as a result, no phase separation occurs. Meanwhile, if the ratio of the biodegradable elastomeric polymer to the water-soluble moisture absorbent is 1: >0.4, excessive phase separation may occur, with the result that the pore size of the porous polymer membrane increases excessively, making it difficult to apply the porous polymer membrane to medical application, cell culture or aesthetic application.

The porous polymer membrane can be fabricated by vapor induced phase separation. Specifically, the porous polymer membrane may be fabricated by applying the mixture solution to a substrate in a closed chamber, followed by spin coating at a relative humidity of 65 to 90%.

The relative humidity is adjusted to the range of 65 to 90%, preferably 70 to 85%, more preferably 72 to 80%, most preferably 74 to 76%, with a solution of a supersaturated salt in water as a non-solvent. If the relative humidity is lower than 65%, the superhydrophobicity of the biodegradable elastomeric polymer may prevent the occurrence of phase separation, and as a result, the porous polymer membrane may not be readily fabricated. Meanwhile, if the relative humidity is higher than 90%, excessive phase separation may occur, with the result that the pore size of the porous polymer membrane increases excessively, making it difficult to apply the porous polymer membrane to medical application, cell culture or aesthetic application. The supersaturated salt can be used for relative humidity control and the degree of hydration of the supersaturated salt may vary depending on the type of the salt. Specifically, the supersaturated salt can be selected from the group consisting of NaCl, $CaCl_2$, $MgCl_2$, $KCO_3$, NaBr, KCl, and mixtures thereof. The supersaturated salt is preferably NaCl, $CaCl_2$ or a mixture thereof, most preferably NaCl. NaCl can be used when the relative humidity is 70 to 80%.

The spin coating may be performed at a speed of 1000 to 4000 rpm, preferably 2000 to 3800 rpm, more preferably 2800 to 3400 rpm, most preferably 3000 rpm, for 10 seconds to 1 minute, preferably 15 seconds to 50 seconds, most preferably 20 seconds to 40 seconds, most preferably 30 seconds. If the spin coating speed is less than 1000 rpm or the coating time is less than 10 seconds, a low porosity and a large thickness (>3 μm) of the membrane may be obtained, rendering the occurrence of cell-cell interaction difficult. Meanwhile, if the spin coating speed exceeds 4000 rpm or the coating time exceeds 1 minute, the thickness of the membrane may be made very small, deteriorating the tensile strength of the membrane.

The porous polymer membrane may have a thickness of 300 nm to 3 μm, a pore size of 100 nm to 5 μm, and a porosity of 20 to 80%. Preferably, the porous polymer membrane has a thickness of 650 nm to 1.2 μm, a pore size of 700 nm to 1.5 μm, and a porosity of 30 to 60%. More preferably, the porous polymer membrane has a thickness of 700 nm to 950 nm, a pore size of 900 nm to 1.2 μm, and a porosity of 35 to 45%. Most preferably, the porous polymer membrane has a thickness of 960 nm, a pore size of 1 μm, and a porosity of 37.

If the thickness of the porous polymer membrane is less than 300 nm, the pore size of the porous polymer membrane is less than 100 nm or the porosity of the porous polymer membrane is less than 20%, active cell-cell interaction may be difficult to induce. Meanwhile, the thickness of the porous polymer membrane exceeds 3 μm, the pore size of the porous polymer membrane exceeds 5 μm or the porosity of the porous polymer membrane exceeds 80%, the elasticity and tensile strength of the porous polymer membrane may deteriorate.

Although not explicitly described in the Examples section that follows, porous polymer membranes were fabricated by varying the kinds of the biodegradable elastomeric polymer and the water-soluble moisture absorbent, the mixing ratio between the biodegradable elastomeric polymer and the water-soluble moisture absorbent, the type of the organic solvent, the relative humidity, and the spin coating conditions, and their elastic moduli and tensile strengths were measured.

As a result, when the following conditions were all met, the porous polymer membranes were found to have thicknesses of 700 to 960 nm, pore sizes of 900 nm to 1.2 μm, and porosities of 35 to 45% and be excellent in elastic modulus and tensile strength, unlike when other conditions and other numerical ranges were employed.

(1) The biodegradable elastomeric polymer is poly(L-lactide-co-caprolactone), poly(L-lactide-co-glycolide) or a mixture thereof, (2) the water-soluble moisture absorbent is LiCl, (3) the organic solvent is tetrahydrofuran, (4) the biodegradable elastomeric polymer is mixed with the water-soluble moisture absorbent in a weight ratio of 1:0.1-0.3 in the organic solvent to prepare the mixture solution, (5) the relative humidity is adjusted to 74 to 76% with a supersaturated salt solution, (6) the spin coating is performed at a speed of 2800 to 3400 rpm for 20 seconds to 40 seconds, and (7) the porous polymer membrane has a thickness of 700 to 960 nm, a pore size of 900 nm to 1.2 μm, and a porosity of 35 to 45%.

When any one of the above conditions was not met, the thicknesses and pore sizes of the porous polymer membranes were not controlled, the elastic moduli and physical strengths (e.g., tensile strengths) deteriorated, making it impossible to apply the porous polymer membranes to medical application, cell culture or aesthetic application.

Although not explicitly described in the Examples section that follows, the thickness, pore size, and porosity of a porous polymer membrane fabricated based on the following conditions were optimized so that cell array and alignment could be controlled more precisely and a uniform culture environment was created over the entire area of the membrane irrespective of the type of cells.

(1) The biodegradable elastomeric polymer is poly(L-lactide-co-caprolactone), (2) the water-soluble moisture absorbent is LiCl, (3) the organic solvent is tetrahydrofuran, (4) the biodegradable elastomeric polymer is mixed with the water-soluble moisture absorbent in a weight ratio of 1:0.2 in the organic solvent to prepare the mixture solution, (5) the relative humidity is adjusted to 75% with a supersaturated salt solution, (6) the spin coating is performed at a speed of 3000 rpm for 30 seconds, and (7) the porous polymer membrane has a thickness of 960 nm, a pore size of 1 μm, and a porosity of 37%.

When any one of the above conditions were not met, it was impossible to precisely control cell array and alignment and it was difficult to provide a uniform culture environment over the entire area of the membrane because the pore size was not uniform.

The present invention provides a porous polymer membrane fabricated by mixing a biodegradable elastomeric polymer with a water-soluble moisture absorbent in an organic solvent to prepare a mixture solution, applying the mixture solution to a substrate in a closed chamber, followed by spin coating at a relative humidity of 65 to 90% wherein the porous polymer membrane has a thickness of 300 nm to 3 μm, a pore size of 100 nm to 5 μm, and a porosity of 20 to 80%.

The porous polymer membrane may be used for medical application, cell culture or aesthetic application. Preferably, the porous polymer membrane is used for medical application or cell culture. Most preferably, the porous polymer membrane is used for cell culture.

The present invention also provides a scaffold for cell culture including the porous polymer membrane.

The present invention also provides a cell culture system including the scaffold for cell culture.

The present invention also provides a method for manufacturing a cell culture system, including: mixing a biodegradable elastomeric polymer with a water-soluble moisture absorbent in an organic solvent to prepare a mixture solution; applying the mixture solution to a substrate in a closed chamber, followed by spin coating at a relative humidity of 65 to 90% to fabricate a porous polymer membrane; removing the water-soluble moisture absorbent contained in the porous polymer membrane; stretching the porous polymer membrane from which the water-soluble moisture absorbent is removed; and placing the stretched porous polymer membrane on cells.

The water-soluble moisture absorbent can be completely removed from the porous polymer membrane by impregnating the porous polymer membrane with water to dissolve the water-soluble moisture absorbent.

The highly elastic porous polymer membrane can be stretched to an appropriate strain for cell alignment or array control. The stretching temperature may be 20 to 40° C. and the strain may be 30 to 60%. Preferably, the stretching temperature is 22 to 35° C. and the strain is 35 to 58%. Most preferably, the stretching temperature is 24 to 26° C. and the strain is 45 to 50%. If the stretching temperature is lower than 20° C. or the strain is lower than 30%, the porous polymer membrane is not sufficiently stretched, making it impossible to control cell alignment or array. Meanwhile, if the stretching temperature is higher than 40° C. or the strain is higher than 60%, the porous polymer membrane is excessively stretched and is thus vulnerable to tearing.

Figure 8:
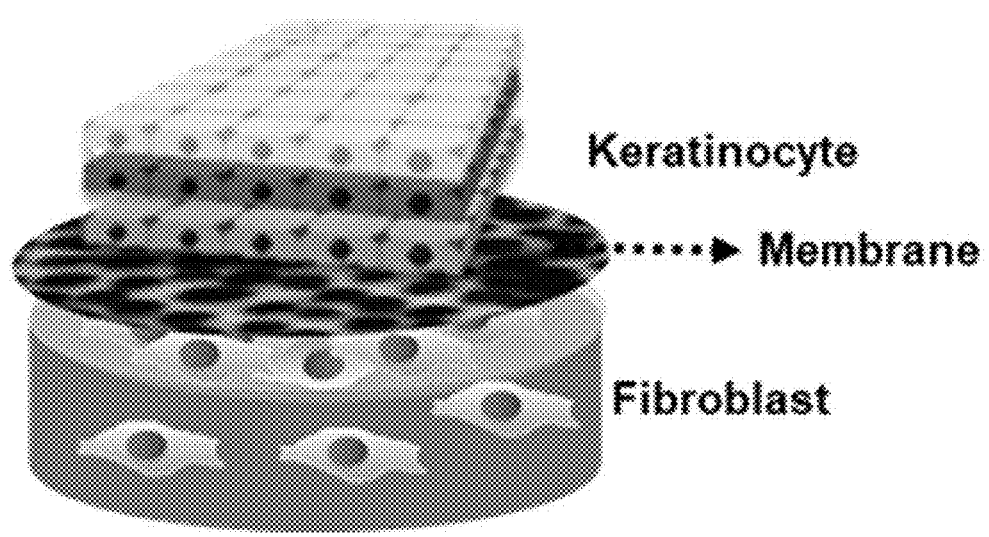
FIG. 8 is a diagram schematically showing the structure of a synthetic skin simulant platform using a porous polymer membrane of the present invention.

FIG. 8 is a diagram schematically showing the structure of a synthetic skin simulant platform using a porous polymer membrane of the present invention. Considering that the differentiation of keratinocytes is an important issue in the synthetic skin simulant platform, a porous polymer membrane can be used to induce hierarchical differentiation of keratinocytes. Particularly, interaction between fibroblasts and keratinocytes is important in the differentiation of keratinocytes. Thus, the porous polymer membrane of the present invention is placed between fibroblasts and keratinocytes to activate interaction between the two different cell types so that differentiation of the keratinocytes can be efficiently induced.

As described above, the porous polymer membrane of the present invention can be fabricated by spin coating a mixture solution containing a biodegradable elastomeric polymer and a water-soluble moisture absorbent in an optimum ratio while maintaining a high relative humidity and has a high porosity, a uniform thickness, and a uniform pore size and is highly elastic. In addition, the thickness and pore size of the porous polymer membrane according to the present invention can be controlled. The porous polymer membrane of the present invention can induce active cell-cell interaction during cell co-culture due to its high porosity. The porous polymer membrane of the present invention enables control over cell alignment or array due to its high biocompatibility and elasticity. Furthermore, the porous polymer membrane of the present invention can be used to in vitro construct a model simulating an in vivo environment, which can find useful applications in tissue engineering. Moreover, the porous polymer membrane of the present invention can be utilized in a platform for inducing stem cell differentiation, a lab-on-a-chip, a synthetic skin simulant platform, etc.

The present invention will be more specifically explained with reference to the following examples but is not limited to these examples.

Example 1

A total of 6 g of poly(lactide-co-caprolactone) (PLCL) as a biodegradable elastomeric polymer and LiCl as a water-soluble moisture absorbent in a weight ratio of 1:0.2 were added to 100 ml of tetrahydrofuran (THF) as an organic solvent to prepare a mixture solution. The two solutes were completely dissolved by vortex mixing for 6 h. The mixture solution was spin coated at 3000 rpm for 30 sec in a closed chamber in which the relative humidity (RH) was adjusted to 75% at 30° C. with a solution of NaCl as a supersaturated salt in water, to fabricate a porous polymer membrane on a glass substrate.

Example 2

A porous polymer membrane was fabricated in the same manner as in Example 1, except that poly(lactide-co-caprolactone) (PLCL) was mixed with LiCl in a weight ratio of 1:0.4.

Comparative Example 1-1

A porous polymer membrane was fabricated in the same manner as in Example 1, except that poly(lactide-co-caprolactone) (PLCL) was used alone without mixing with the water-soluble moisture absorbent LiCl.

Comparative Example 1-2

A porous polymer membrane was fabricated in the same manner as in Example 1, except that poly(lactide-co-caprolactone) (PLCL) was mixed with LiCl in a weight ratio of 1:0.6.

Comparative Examples 2-1 to 2-4

Mixture solutions were prepared as described in Example 1, except that poly(lactide-co-caprolactone) (PLCL) was mixed with LiCl in different ratios of 1:0 (Comparative Example 2-1), 1:0.2 (Comparative Example 2-2), 1:0.4 (Comparative Example 2-3), and 1:0.6 (Comparative Example 2-4) in tetrahydrofuran (THF) as an organic solvent. The two solutes were completely dissolved by vortex mixing for 6 h. Each of the mixture solutions was spin coated at 3000 rpm for 30 sec in a closed chamber in which the relative humidity (RH) was adjusted to 29% at 30° C. with a solution of $CaCl_2$ as a supersaturated salt in water, to fabricate a porous polymer membrane on a glass substrate.

Figure 4:
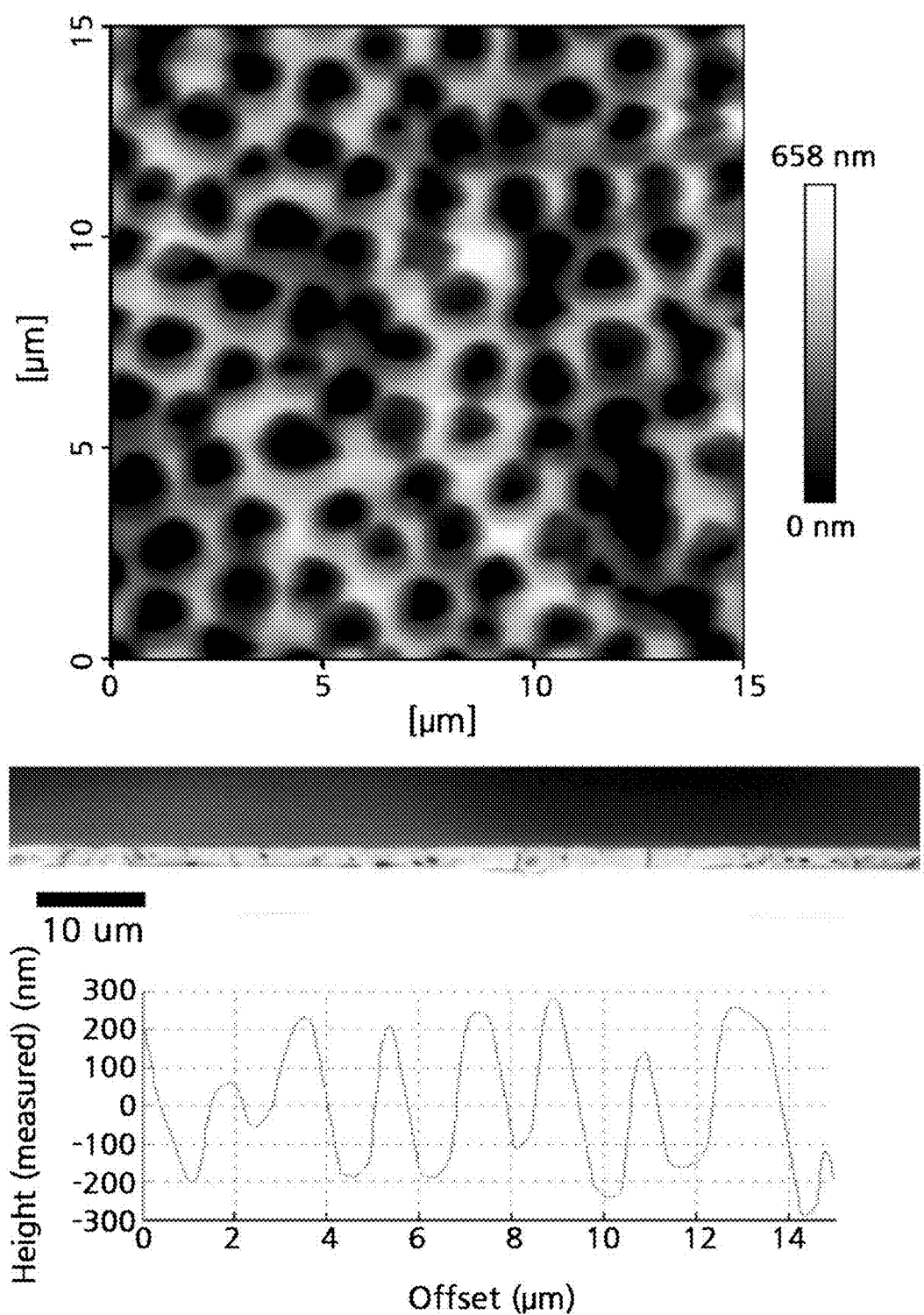
FIG. 4 shows the results of atomic force microscopy for a porous polymer membrane fabricated in Example 1.

Experimental Example 1-1: Analysis of Surface Morphologies and Porous Structures of the Porous Polymer Membranes The surface morphologies and porous structures of the porous polymer membranes fabricated in Examples 1 and 2 and Comparative Examples 1-1, 1-2, 2-1, and 2-4 were analyzed by scanning electron microscopy (SEM) and atomic force microscopy (AFM), and the results are shown in FIGS. 3 and 4, respectively.

FIG. 3 shows SEM images showing the surface morphologies of the porous polymer membranes fabricated in Examples 1 and 2 and Comparative Examples 1-1, 1-2, and 2-1 to 2-4. Referring to FIG. 3, the porous polymer membranes of Examples 1 and 2, which were fabricated by mixing PCLC with LiCl in weight ratios of 1:0.2 and 1:0.4 at a high relative humidity (RH) of 75%, respectively, were confirmed to have uniform pore sizes. When the ratio of PCLC to LiCl was 1:0.4, the pore size was larger. The thickness, pore size, and porosity of the porous polymer membrane of Example 1 were 960 nm, 1 μm, and 37%, respectively. The thickness, pore size, and porosity of the porous polymer membrane of Example 2 were 816 nm, 5 μm, and 68%, respectively.

In contrast, the porous polymer membrane of Comparative Example 1-1, which was fabricated using PLCL alone, had no porous structure. The excess water-soluble moisture absorbent LiCl caused excessive water absorption in the porous polymer membrane of Comparative Example 1-2, and as a result, extreme phase separation occurred, failing to make the membrane freestanding. It was overall difficult to obtain porous structures of the membranes of Comparative Examples 2-1 to 2-4 irrespective of the mixing ratio between the biodegradable elastomeric polymer and the water-soluble moisture absorbent due to the low relative humidity (RH) in the chamber.

These results demonstrate that the pore size of the inventive porous polymer membrane can be controlled by varying both the relative humidity and the mixing ratio between the biodegradable elastomeric polymer and the water-soluble moisture absorbent.

FIG. 4 shows the results of atomic force microscopy for the porous polymer membrane fabricated in Example 1. Referring to FIG. 4, a plurality of uniformly sized pores were uniformly distributed on the surface of the porous polymer membrane. Data on a side cross-sectional AFM image of the porous polymer membrane are graphically shown in FIG. 4. The graph reveals that a plurality of pores were uniformly distributed over the entire area of the membrane.

Experimental Example 1-2: Analysis of Cell Morphologies on and Porous Structures of Porous Polymer Membranes Porous polymer membranes were fabricated in the same manner as in Example 1, except that the spin speed was changed to 1000 and 2000 rpm. The thicknesses of the porous polymer membranes fabricated by spin coating at the different speeds of 1000, 2000, and 3000 rpm were measured. The results are shown in FIG. 5.

Figure 5:
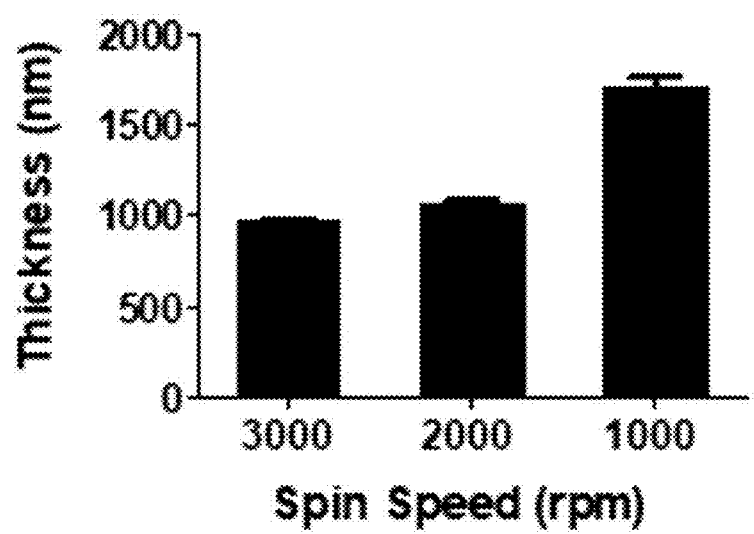
FIG. 5 shows the thicknesses of porous polymer membranes fabricated by spin coating at different speeds in Example 1 and Experimental Example 1-2.

FIG. 5 shows the thicknesses of the porous polymer membranes fabricated by spin coating at the different speeds. Referring to FIG. 5, the thicknesses of the membranes were 960 nm, 1 µm, and 1.75 µm when the spin speeds were 3000 rpm, 2000 rpm, and 1000 rpm, respectively. These results demonstrate that the thickness of the inventive porous polymer membrane can be controlled by varying the spin coating speed. The most optimal thickness of the inventive membrane was obtained when the spin speed was 3000 rpm.

Experimental Example 2-1: Evaluation of Cell Viabilities on the Porous Polymer Membrane The biocompatibility of the porous polymer membrane fabricated in Example 1 was evaluated by the following procedure. The porous polymer membrane was impregnated with water to dissolve the water-soluble moisture absorbent contained in the membrane. After removal of the water in which the water-soluble moisture absorbent (LiCl) was dissolved, the porous polymer membrane was separated from the substrate. The separated porous polymer membrane was stretched to 30% of its original length and fixed to a PET ring or Transwell insert, as shown in FIG. 1. Then, the fixed porous polymer membrane was evaluated for cell viability for 7 days by a standard live/dead assay. The results are shown in FIG. 6.

Figure 6:
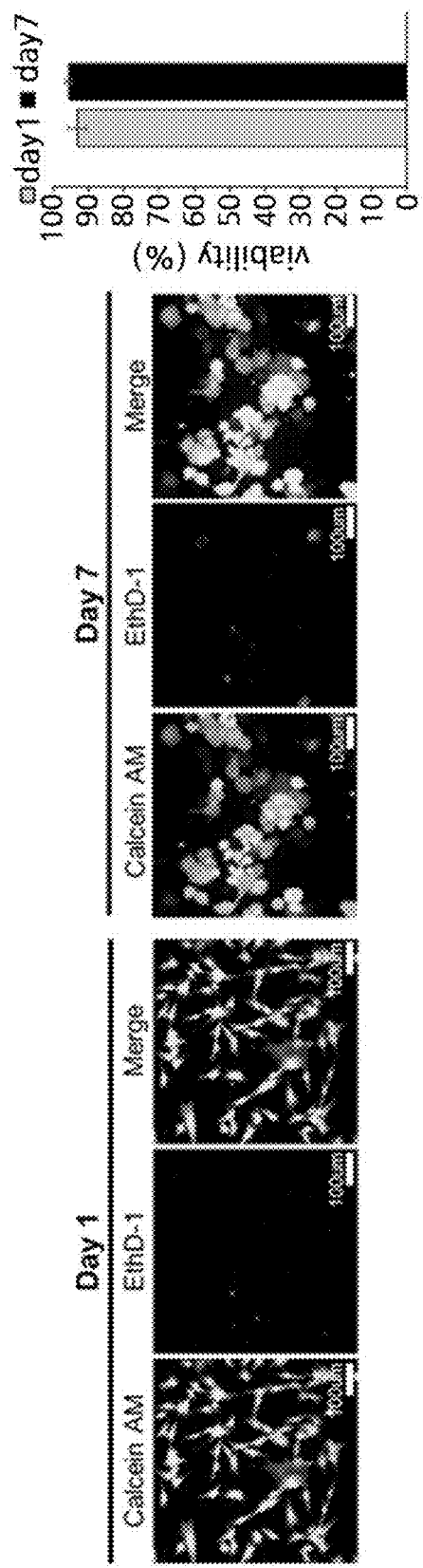
FIG. 6 shows the viabilities of cells in a porous polymer membrane fabricated in Example 1, which were evaluated by a live/dead assay.

FIG. 6 shows the viabilities of cells in the porous polymer membrane fabricated in Example 1, which were evaluated by a live/dead assay. In FIG. 6, the green color indicates live cells and the red color indicates dead cells. The cell viability at day 1 was maintained at a level similar to that at 7 days, demonstrating high biocompatibility of the porous polymer membrane. Therefore, the porous polymer membrane is expected to find a variety of applications, including scaffolds for cell culture, cell culture systems, and artificial skin.

Experimental Example 2-2: Evaluation of Cell Alignments on the Porous Polymer Membrane Stretched to Different Strains The procedure of Experimental Example 2-1 was repeated except that the porous polymer membrane was stretched to different stains of 0, 30, and 60%. Cell alignments on the stretched porous polymer membranes were confirmed. The results are shown in FIG. 7.

Figure 7:
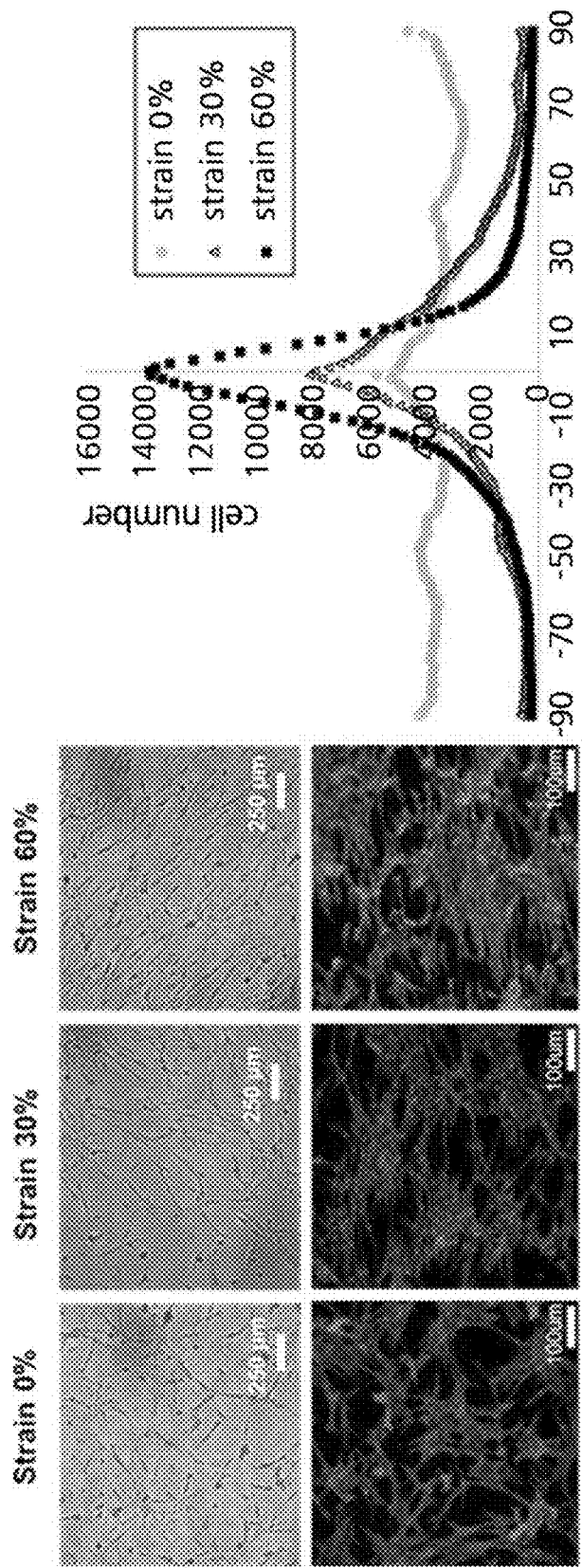
FIG. 7 shows cells aligned on porous polymer membranes stretched to different strains in Experimental Example 2-2.

FIG. 7 shows cells aligned on the stretched porous polymer membranes. Referring to FIG. 7, different cell alignments were observed on the porous polymer membranes stretched to different strains. The cell alignment directions were quantified and are graphically shown in FIG. 7. As the strain increased, the number of cells aligned in a constant direction increased. Particularly, the number of cells aligned on the membrane stretched to a strain of 60% was much larger than that of cells aligned on the membrane stretched to a strain of 0%.

What is claimed is:

1. A method for fabricating a porous polymer membrane, comprising:
    mixing a biodegradable elastomeric polymer with a water-soluble moisture absorbent in an organic solvent to prepare a mixture solution; and
    applying the mixture solution to a substrate in a closed chamber, followed by spin coating at a relative humidity of 65 to 90%,
    wherein the biodegradable elastomeric polymer is poly (L-lactide-co-caprolactone),
    wherein a molar ratio of the L-lactide to the caprolactone in the poly(L-lactide-co-caprolactone) is 1-9:9-1,
    wherein the poly(L-lactide-co-caprolactone) has
        a number average molecular weight (Mn) of 50,000 to 500,000 g/mol, and
        a weight average molecular weight (Mw) of 50,000 to 800,000 g/mol,
    wherein a strain of the porous polymer membrane is 30 to 60% at a stretching temperature of 20 to 40° C.

2. The method according to claim 1, wherein the water-soluble moisture absorbent is selected from the group consisting of LiCl, $CaCl_2$, $ZnCl_2$, KOH, NaOH, $MgCl_2$, $FeCl_3$, $K_2CO_3$, and mixtures thereof.

3. The method according to claim 1, wherein the organic solvent is selected from the group consisting of tetrahydrofuran, dimethylformamide, diethylformamide, N-methyl-2-pyrrolidone, dimethyl sulfoxide, dimethylacetamide, methanol, ethanol, chloroform, dichloromethane, and mixtures thereof.

4. The method according to claim 1, wherein the biodegradable elastomeric polymer is mixed with the water-soluble moisture absorbent in a weight ratio of 1:0.05-0.4 in the organic solvent to prepare the mixture solution.

5. The method according to claim 1, wherein the relative humidity is adjusted to 70 to 85% with a supersaturated salt solution.

6. The method according to claim 1, wherein the spin coating is performed at a speed of 1000 to 4000 rpm for 10 seconds to 1 minute.

7. The method according to claim 1, wherein the porous polymer membrane has a thickness of 300 nm to 3 µm, a pore size of 100 nm to 5 µm, and a porosity of 20 to 80%.

8. The method according to claim 1, wherein the biodegradable elastomeric polymer is poly(L-lactide-co-caprolactone), poly(L-lactide-co-glycolide) or a mixture thereof, the water-soluble moisture absorbent is LiCl, the organic solvent is tetrahydrofuran, the biodegradable elastomeric polymer is mixed with the water-soluble moisture absorbent in a weight ratio of 1:0.1-0.3 in the organic solvent to prepare the mixture solution, the relative humidity is adjusted to 74 to 76% with a supersaturated salt solution, the spin coating is performed at a speed of 2800 to 3400 rpm for 20 seconds to 40 seconds, and the porous polymer membrane has a thickness of 700 nm to 960 nm, a pore size of 900 nm to 1.2 μm, and a porosity of 35 to 45%.

9. The method according to claim 8, wherein the biodegradable elastomeric polymer is poly(L-lactide-co-caprolactone), the water-soluble moisture absorbent is LiCl, the organic solvent is tetrahydrofuran, the biodegradable elastomeric polymer is mixed with the water-soluble moisture absorbent in a weight ratio of 1:0.2 in the organic solvent to prepare the mixture solution, the relative humidity is adjusted to 75% with a supersaturated salt solution, the spin coating is performed at a speed of 3000 rpm for 30 seconds, and the porous polymer membrane has a thickness of 960 nm, a pore size of 1 μm, and a porosity of 37%.

* * * * *